(12) United States Patent
     Heitel

(10) Patent No.: US 9,724,238 B2
(45) Date of Patent: Aug. 8, 2017

(54) OPHTHALMIC INTERFACE APPARATUS, METHOD OF INTERFACING A SURGICAL LASER WITH AN EYE, AND SUPPORT RING FOR USE WITH A SUCTION RING

(71) Applicant: AMO Development, LLC., Santa Ana, CA (US)

(72) Inventor: Robert Heitel, Laguna Beach, CA (US)

(73) Assignee: AMO Development, LLC, Santa Ana, CA (US)

( * ) Notice: Subject to any disclaimer, the term of this patent is extended or adjusted under 35 U.S.C. 154(b) by 490 days.

(21) Appl. No.: 14/089,326

(22) Filed: Nov. 25, 2013

(65) Prior Publication Data
US 2014/0222050 A1    Aug. 7, 2014

Related U.S. Application Data

(60) Provisional application No. 61/732,010, filed on Nov. 30, 2012, provisional application No. 61/732,002, filed on Nov. 30, 2012.

(51) Int. Cl.
  *A61F 9/00* (2006.01)
  *A61F 9/009* (2006.01)
(52) U.S. Cl.
  CPC .................................. *A61F 9/009* (2013.01)
(58) Field of Classification Search
  CPC .......... A61F 9/007; A61F 9/008; A61F 9/009; A61F 2009/00872; A61F 2009/00846; A61F 9/013; A61F 9/00802; A61F 9/00781; A61F 2009/0087; A61F 2009/00887; A61F 2009/00865; A61F 2009/00889; A61F 2009/0052; A61F 2/147; A61F 2/15; A61B 2017/306; A61B 3/117
  USPC ......................................................... 606/166
  See application file for complete search history.

(56) References Cited

U.S. PATENT DOCUMENTS

| | | | |
|---|---|---|---|
| 5,772,675 A * | 6/1998 | Hellenkamp | ................. 606/166 |
| 6,863,667 B2 | 3/2005 | Webb et al. | |
| 2002/0103481 A1 * | 8/2002 | Webb | ..................... A61F 9/009 606/5 |

(Continued)

*Primary Examiner* — Katherine M Shi
*Assistant Examiner* — Mohamed Gabr
(74) *Attorney, Agent, or Firm* — Abbott Medical Optics Inc.

(57) ABSTRACT

Apparatus and methods are provided for interfacing a surgical laser with an eye using a patient interface device that minimizes aberrations through a combination of a contact lens surface positioning and a liquid medium between an anterior surface of the eye and the contact lens surface. Further, support rings, ocular stability devices, and methods for interfacing an eye during laser surgery are provided. In an embodiment, by way of example only, a support ring includes a first end surface, a second end surface opposite the first end surface, and an outer surface extending between the first end surface and the second end surface. The second end surface has a width that is greater than a width of the first end surface and extends toward a central opening in the support ring to define a concave curvature configured to substantially match a curvature of a patient's eye. The outer surface includes an annular groove formed adjacent the first end surface and a plurality of exterior vacuum channels spaced around the annular groove and extends axially from the annular groove to the second end surface.

18 Claims, 13 Drawing Sheets

(56) References Cited

U.S. PATENT DOCUMENTS

2009/0172819 A1 7/2009 Pruden et al.
2013/0103009 A1* 4/2013 Gooding ........................ 606/4

* cited by examiner

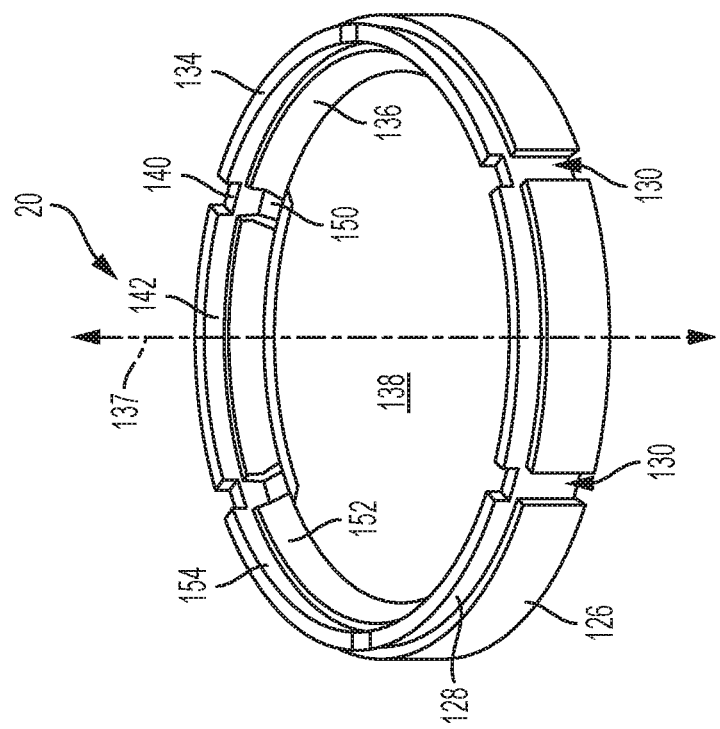
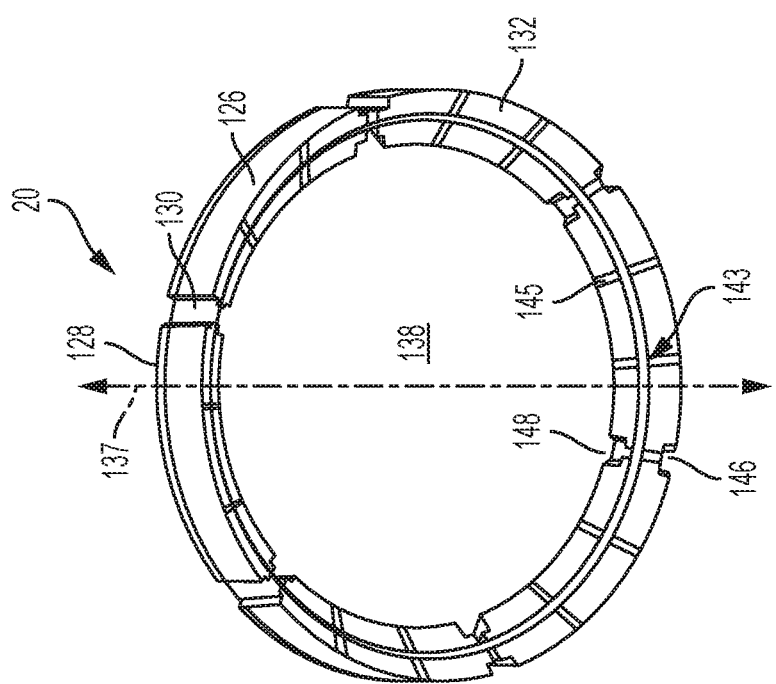
FIG. 13
FIG. 12

OPHTHALMIC INTERFACE APPARATUS, METHOD OF INTERFACING A SURGICAL LASER WITH AN EYE, AND SUPPORT RING FOR USE WITH A SUCTION RING

CROSS REFERENCE TO RELATED APPLICATIONS

This application claims the benefit of priority to U.S. Provisional Application Ser. No. 61/732,010, filed Nov. 30, 2012, and 61/732,002, filed Nov. 30, 2012, the entirety of which are hereby incorporated by reference.

FIELD OF THE INVENTION

The present invention relates in general to ophthalmic laser surgery and, more particularly, to an ophthalmic interface apparatus used to stabilize the eye of a patient with respect to a laser beam during ophthalmic surgery, a support ring for use with a suction ring of an ophthalmic or ocular interface device used to stabilize the eye of a patient with respect to a laser beam during ophthalmic surgery, and methods of interfacing the eye with a surgical laser during laser surgery, including methods of interfacing the eye using the support ring.

BACKGROUND

In recent years, significant developments in laser technology have led to its application in the field of ophthalmic surgery. In particular, laser surgery has become the technique of choice for ophthalmic surgical applications. In certain ophthalmic laser procedures, surgeons use a mechanical device termed a microkeratome to cut a layer of the anterior surface of the cornea in order to expose the underlying corneal stroma to which the laser is applied. However, complications surrounding the use of the microkeratome with a metal blade have resulted in research into improved techniques that are performed exclusively by a laser system.

Laser refractive surgeries are performed routinely to treat myopia, hyperopia, astigmatism, and other conditions which cause a patient to rely on vision correction devices (such as contacts and/or glasses) to see. Such procedures include LASIK (Laser Assisted In-Situ Keratomileusis), PRK (Photo Refractive Keratectomy) and LASEK (Laser Sub-epithelial Keratomileusis) procedures, which use an excimer laser to re-shape a curvature of a patient's cornea through tissue ablation. In many cases, laser refractive surgeries eliminate or greatly reduce the patient's reliance on vision correction devices. Such all-laser techniques provide significant improvements over conventional mechanical devices.

Despite these advances in laser technology, the use of such systems for ophthalmic surgical procedures remains fraught with substantial mechanical limitations, particularly in the area of developing a stable interface between an incident laser beam and the eye of a patient. Ophthalmic surgery is a precision operation and requires precise coupling between the surgical tool (i.e., the laser beam) and the region to be disturbed (i.e., a portion of the patient's eye). Movement of the eye with respect to the intended focal point of the laser beam can lead to non-optimal results and might result in permanent damage to non-renewable tissue within the eye. Given that eye movement is often the result of autonomic reflex, techniques have been developed in an attempt to stabilize the position of a patient's eye with respect to an incident laser beam.

For instance, prior to surgery, the patient's eye is stabilized to prevent translation movement and rotation. In particular, an interface device including a suction ring is placed against sclera tissue of the eye. The suction ring provides a suction pressure to the eye to create a fixation force between the interface device and the eye. After the eye is stabilized, a femtosecond laser is positioned over the interface device and is used to form laser incisions in the corneal tissue to reveal a corneal flap. A surgeon folds over the corneal flap to expose stromal tissue. Next, the surgeon uses the excimer laser to pulse a beam of laser energy onto the exposed stromal tissue. Each pulse removes a very small and precise amount of corneal tissue so that the total removal of tissue alters and corrects the refractive properties of the overall eye. After irrigation with a saline solution, the surgeon folds the corneal flap back in place to adhere to the underlying stromal tissue.

Mechanical stabilization devices have been proposed, for example, a corneal applanation device, which is the subject of U.S. patent application Ser. No. 09/172,819, filed Oct. 15, 1998 (herein incorporated by reference in its entirety), and commonly owned by the assignee of the present invention. Such a mechanical device directly couples a patient's eye to the laser's delivery system being affixed to both the laser and the anterior surface of a patient's cornea. The corneal coupling, in these devices, is typically implemented by lowering an applanation fixture over the anterior surface of the cornea under pressure. Another example stabilization and applanation device is described in U.S. Pat. No. 6,863,667, also herein incorporated by reference in its entirety. It is assumed in these forms of devices that pressure applied normal to the corneal surface will restrict conventional motion of the cornea thereby stabilizing the eye along a major access normal to the device.

However, although this assumption may hold true in a large number of cases, it certainly does not have universal application. Moreover, in the cases where it does hold, the device/cornea interface should be established with the iris centered, for best results. The actual establishment of an effective device/corneal interface is an exercise in trial-and-error, resulting in a great deal of frustration to doctor and patient, as well as considerable eye fatigue.

For ophthalmic laser procedures where eye tissue is to be photodisrupted, it is desirable to have proper focus of the laser beam to a specific focal spot in the tissue that is to be effected. Proper focus includes focal definition and proper dimensionality (i.e., the correct spot diameter and shape). To this end, it is helpful for the laser beam to be as free from aberrations as possible. In particular, for ophthalmic laser procedures involving the cornea, the spherical geometry of the cornea can introduce optical aberrations by its shape, and these are separate and distinct from aberrations that may be introduced by the laser optical system. Corneal induced aberrations can distort the definition of the focal spot of a laser beam as the beam is focused to a position within corneal tissue or deeper into the eye, such as the capsular bag or the natural lens.

Due to the spherical geometry of the anterior surface of the cornea, two specific types of aberrations are of particular importance with regard to beam distortion; spherical aberration (which relates to points on the optical axis of the laser beam) and coma which relates to points that are off-axis). Spherical aberration and coma are similar to one another in that they both arise from a failure to image or focus optical ray traces onto the same point. Spherical aberration relates to a distortion that can be characterized as radial in nature, with some radial directions being stretched while other radial directions are shrunk, converting thereby an ideally circular spot into an elliptical spot. Coma distortion, on the other hand, implies an elongation along one radius a circle, resulting in a "comet-like" shape. Accordingly, any structure which interfaces between a curved, anterior surface of the cornea and laser delivery system will likely encounter such aberration concerns.

In view of the foregoing, it is thus evident that there is a need for a simple mechanical interface device that is able to stabilize the eye against relative motion with respect to a laser beam used for ophthalmic surgical procedures without relying on secondary mechanical considerations, such as surface tension, friction, or the like. Such a device should be able to present an optical feature to an incident laser beam in a stable, well characterized location. In addition to maintaining a proper orientation between the eye and a laser delivery system during ophthalmic laser surgery, such a device should minimize intraocular pressure during the surgical procedure. Such a device should be easy for a clinician to affix, as well as being simple and cost effective to manufacture and use.

Furthermore, although laser refractive surgeries are typically performed without long-lasting side effects, in some instances, the suction pressure applied during stabilization may affect one patient more than another. For example, though the suction pressure delivered to a patient's eye is typically confined within an area defined by an outer diameter of the suction ring, some patients may experience suction pressure outside of the cornea to the conjunctiva. In such cases, the suction pressure may apply a negative relative pressure to the conjunctiva to deform the globe of the eye resulting in ruptured blood vessels, reddening of the conjunctiva post-surgery, and/or an increased intraocular pressure.

SUMMARY OF THE INVENTION

Accordingly, embodiments of this invention provide apparatus and methods for interfacing a surgical laser with an eye. In one embodiment, a patient interface device is provided that minimizes aberrations through a combination of a contact lens surface positioning and a liquid medium between an anterior surface of the eye and the contact lens surface. In one embodiment, an interface for coupling a patient's eye to a surgical laser system includes an attachment ring configured to overlay the anterior surface of the eye, the attachment ring comprising an inner surface that defines a chamber when overlaid on the anterior surface of the eye, the chamber configured to receive a liquid. The interface also includes a lens cone configured to couple to a delivery tip of the surgical laser system, wherein the attachment ring and lens cone include a splined interface for coupling to each other. In another embodiment, a second aspheric lens is located in the interface, above the contact lens surface.

In other embodiments of the invention, support rings, ocular stability devices, and methods for interfacing an eye during laser surgery are provided that reduce intraocular pressure and minimize the effects of suction pressure on the eye. In one embodiment, a support ring for use with a suction ring of an ocular stability device includes a first end surface, a second end surface opposite the first end surface, and an outer surface extending between the first end surface and the second end surface. The second end surface has a width that is greater than a width of the first end surface and extends toward a central opening in the support ring to define a concave curvature configured to substantially match a curvature of a patient's eye. The outer surface includes an annular groove formed adjacent the first end surface and a plurality of exterior vacuum channels spaced around the annular groove and extends axially from the annular groove to the second end surface.

In another embodiment, the ocular stability device includes a suction ring and a support ring. The suction ring includes an outer annular wall, an inner annular wall, a radial surface extending between the outer annular wall and the inner annular wall defining a cavity, and a tube extending radially outwardly from the outer annular wall defining an orifice in communication with the cavity. The support ring is disposed in the cavity and defines a central opening. The support ring includes a first end surface, a second end surface opposite the first end surface, and an outer surface extending between the first end surface and the second end surface. The second end surfaces has a width that is greater than a width of the first end surface and extends toward the central opening of the support ring to define a concave curvature configured to substantially match a curvature of a patient's eye. The outer surface includes an annular groove and a plurality of exterior vacuum channels. The annular groove is formed adjacent the first end surface in communication with the orifice. The plurality of exterior vacuum channels is spaced around the annular groove and extending axially from the annular groove to the second end surface.

In another embodiment, a method includes contacting a support ring to an anterior surface of the eye. The support ring being is in a cavity of a suction ring. The cavity is defined between an outer annular wall, an inner annular wall, and a radially extending wall of the suction ring. The support ring includes a first end surface, a second end surface opposite the first end surface, and an outer surface. The second end surface has a width that is greater than a width of the first end surface for contacting the eye and extends toward a central opening of the support ring to define a concave curvature configured to substantially match a curvature of the eye. The outer surface extends between the first end surface and the second end surface. The outer surface includes an annular groove and a plurality of exterior vacuum channels. The annular groove is formed adjacent the first end surface, and the plurality of exterior vacuum channels are spaced around the annular groove and extending axially from the annular groove to the second end surface. The method also includes applying a vacuum suction to the anterior surface of the eye via an orifice extending from the suction ring, the orifice being in communication with the annular groove and the plurality of exterior vacuum channels.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

Ophthalmic Interface Apparatus

So that the advantages of the embodiments of this invention will be readily understood, a more particular description of the embodiments of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

Support Ring for Use with a Suction Ring

Figure 2:
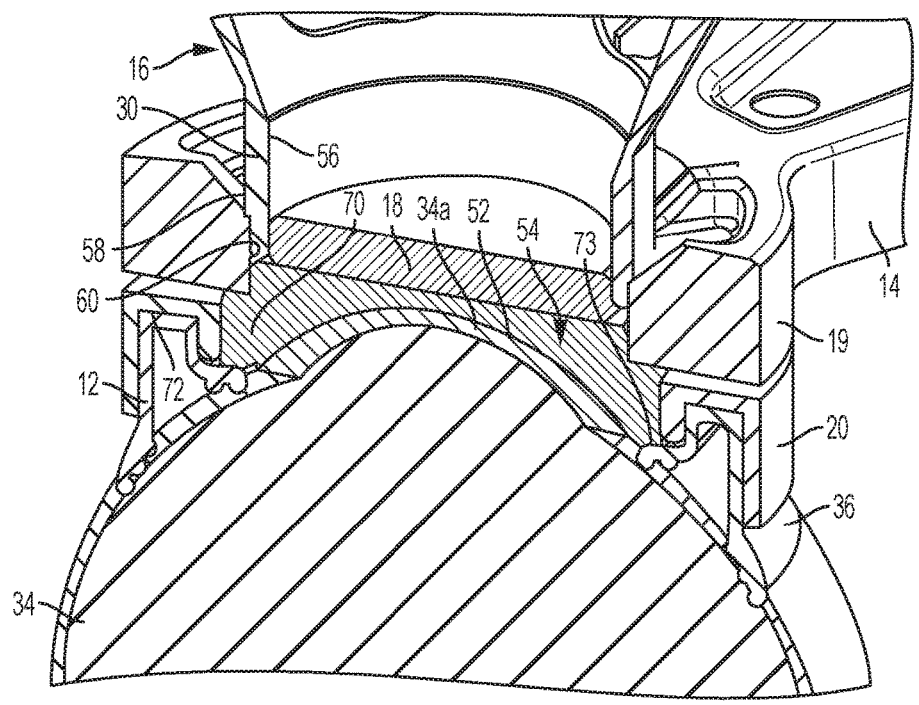
FIG. 2 is a cross-sectional illustration of the ocular stabilization device of FIG. 1, showing operation of the device to interface with the corneal surface of an eye known in the art.
Figure 8:
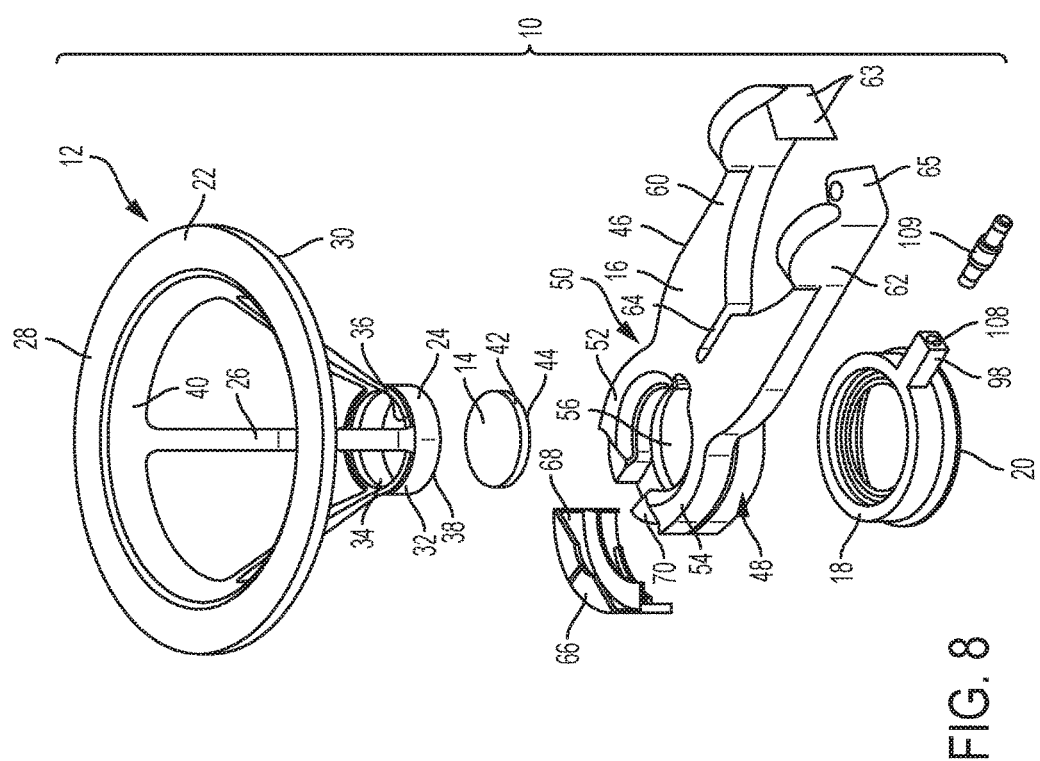
Figure 9:
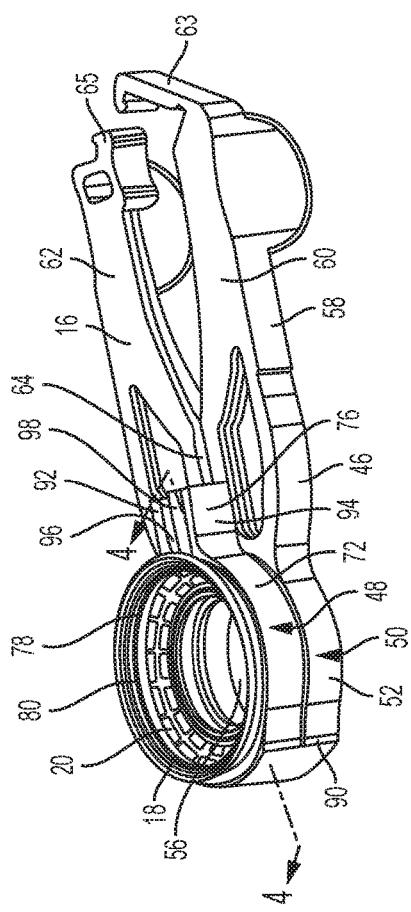
Figure 10:
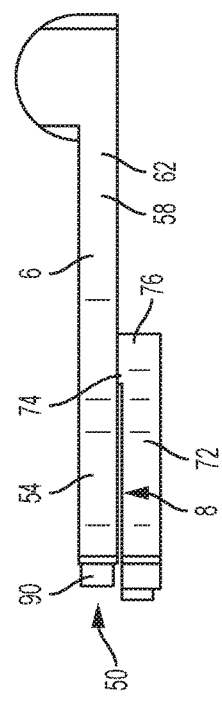
Figure 11:
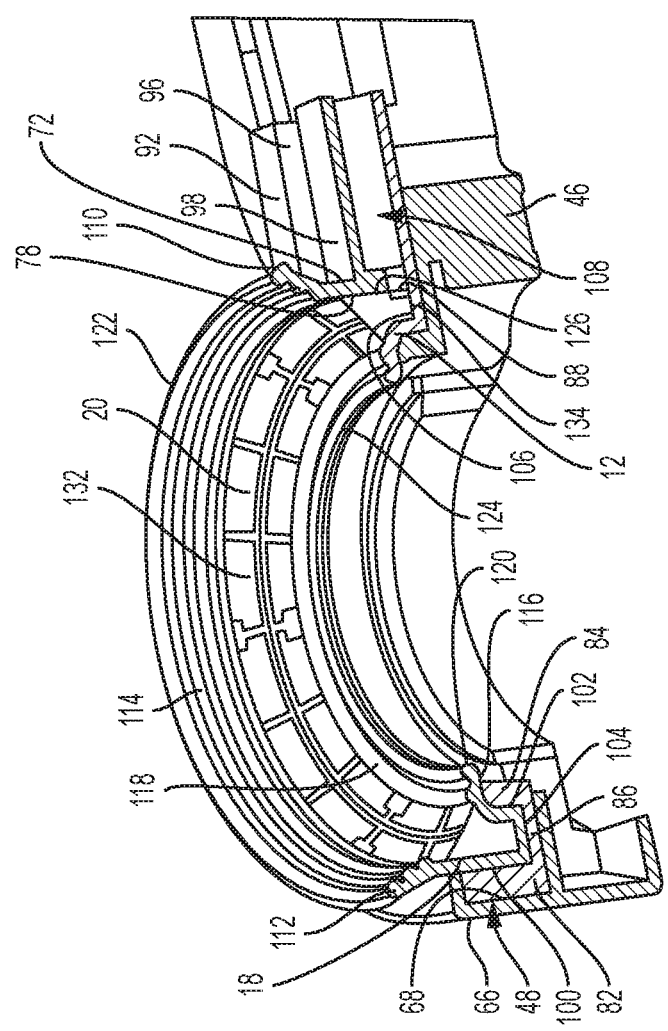
Figure 14:
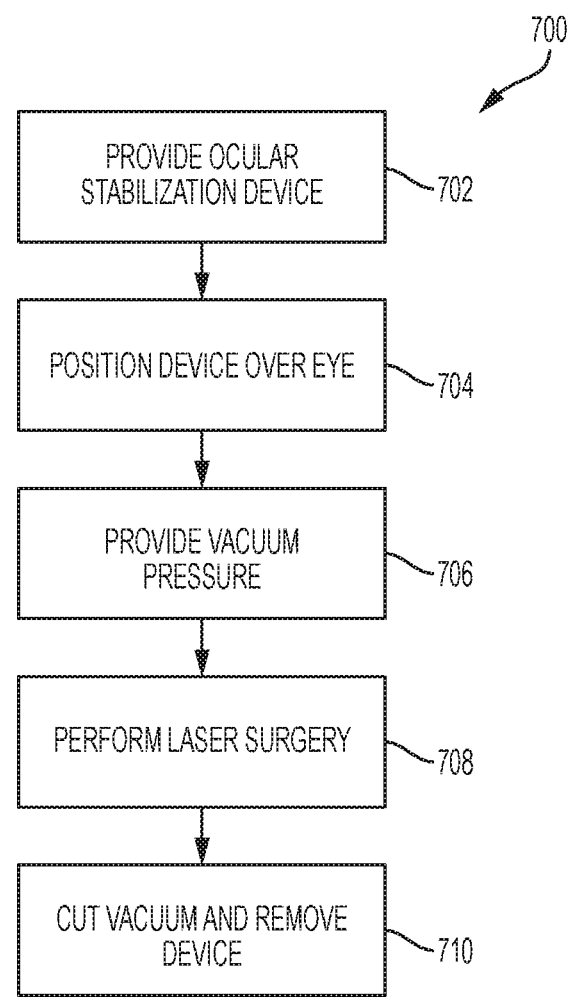
Figure 15:
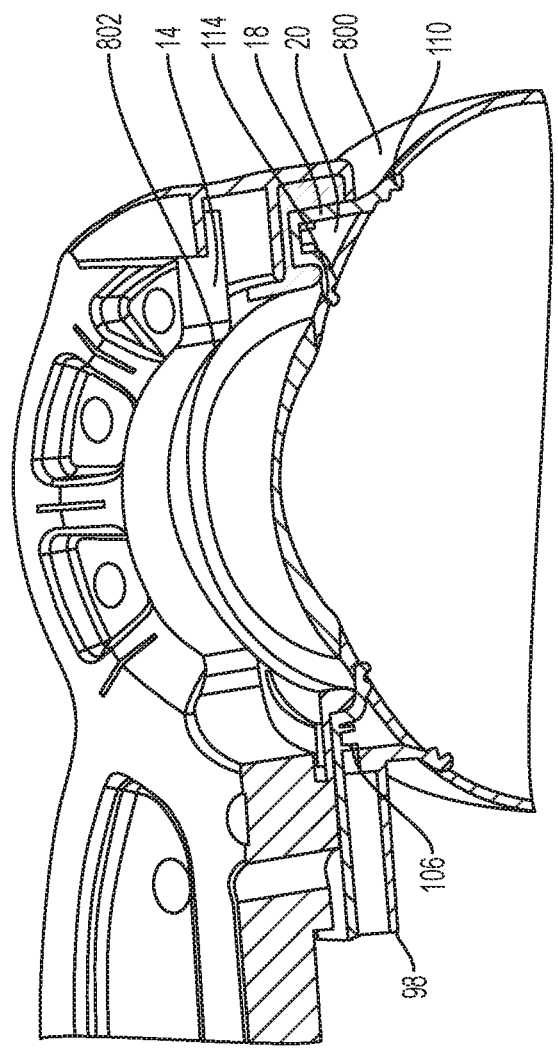

FIG. 8 is an exploded, perspective view illustration of an ocular stabilization device in accordance with one embodiment of the present invention;

FIG. 9 is a bottom, perspective view illustration of a gripper component, a suction ring, and a support ring, in accordance with an embodiment of the present invention;

FIG. 10 is a simplified, side view illustration of a gripper component, a suction ring, and a support ring, in accordance with an embodiment of the present invention;

FIG. 11 is cross-sectional view illustration of a portion of a gripper component, a suction ring, and a support ring taken along line 4-4 in FIG. 2, in accordance with an embodiment of the present invention;

FIG. 12 is a bottom, perspective view illustration of a support ring, in accordance with an embodiment of the present invention;

FIG. 13 is a top, perspective view illustration of a support ring, in accordance with an embodiment of the present invention;

FIG. 14 is a flow diagram of a method of interfacing with an eye during a laser surgery, in accordance with an embodiment of the present invention; and FIG. 15 is a cross-sectional view illustration of a portion of an ocular stabilization device component disposed over an eye, in accordance with an embodiment of the present invention.

DETAILED DESCRIPTION OF THE DRAWINGS

The following detailed description is merely exemplary in nature and is not intended to limit the inventive subject matter or the application and uses of the inventive subject matter. Certain terminology may also be used in the following description for the purpose of reference only, and thus are not intended to be limiting. For example, terms such as "anterior," "inner," "outer," and "top" may refer to direction in the drawings to which reference is made and/or the orientation or location of portions of the components within a consistent but arbitrary frame of reference which is made clear by reference to the text and the associated drawings describing the component under discussion. Such terminology may include the words specifically mentioned above, derivatives thereof, and words of similar import.

Ophthalmic Interface Apparatus and Method of Interfacing a Surgical Laser with an Eye Conceptually, the present invention is directed to a mechanical apparatus that performs the functions of coupling the anterior surface of a target eye to a surgical laser and stabilizing the eye. The apparatus is termed mechanical because it directly couples the mechanical surface of an operative target, such as human corneal tissue, to a mechanical fixture of a surgical laser system, such as the distal tip of a laser beam's delivery system. Simply put, and in the context of a particular embodiment which will be described in greater detail below, the apparatus is affixed to the anterior surface of a human eye and is affixed to the laser delivery system.

Figure 1:
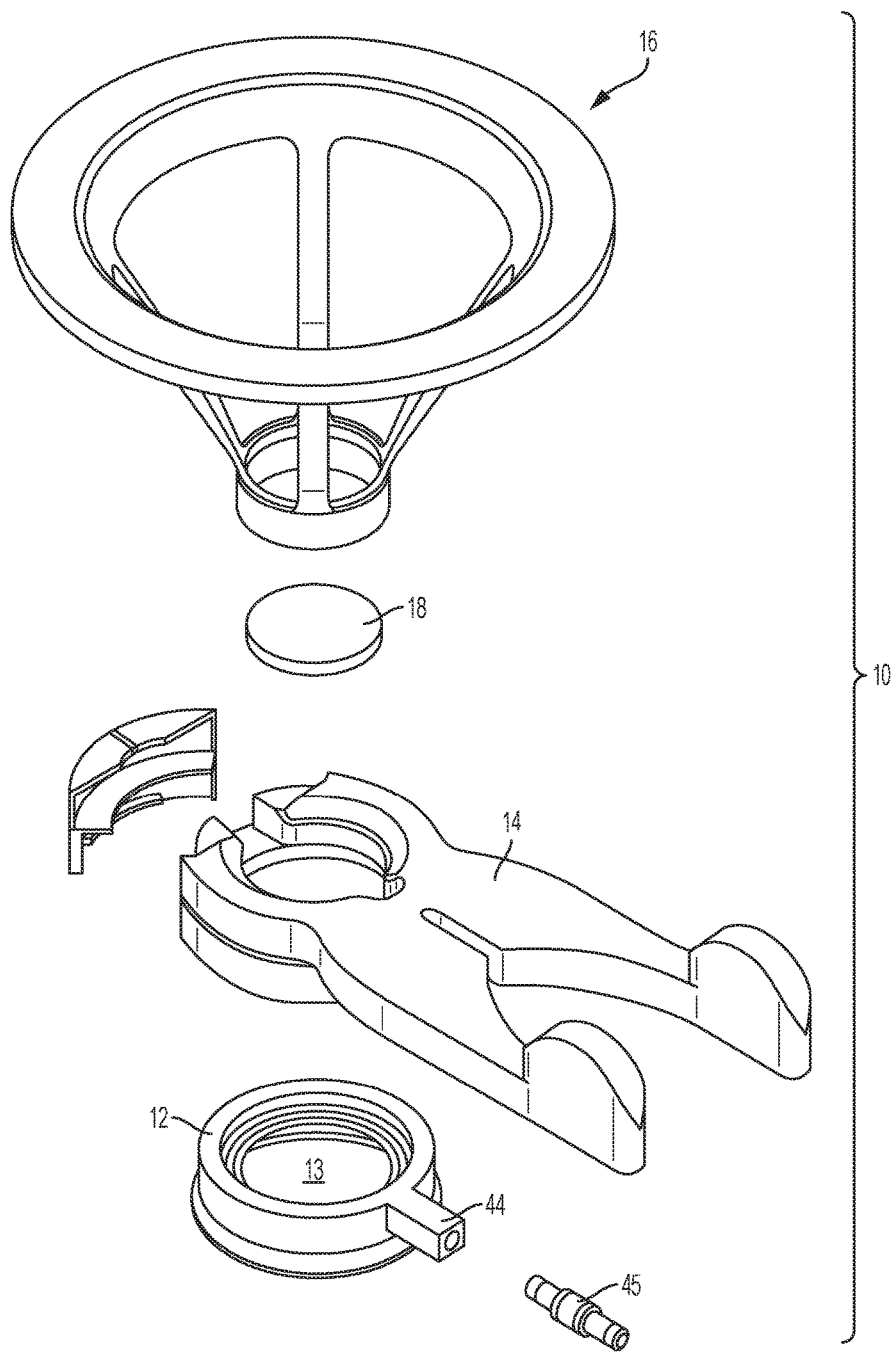
FIG. 1 is an exploded, perspective illustration of the component portions of an ocular stabilization device known in the art.

Referring initially to FIG. 1, an illustrative ocular stabilization device known in the art is shown in an exploded, perspective view, and is generally indicated at 10. The ocular stabilization device (referred to herein as simply a patient interface) is an apparatus that attaches to a human eye and holds (fixes) the eye in all three axes (x, y and z) from translational and rotational movement with respect to the incident beam of a laser surgical device. In addition, the stabilization device may allow for the cornea of the eye to be applanated by a lens (laser optic) in one embodiment. The stabilization device grips, holds or affixes the eye to the applanation lens, or laser optic, during a laser surgical procedure, so as to minimize or preclude differential motion of the human eye with respect to the laser optical path during the laser procedure.

With regard to FIG. 1, the stabilization device 10 is comprised of a number of component parts that may be disposable (i.e., used once and discarded) and/or re-usable. In this regard, the stabilization device 10 suitably comprises an ocular attachment ring 12, by means of which the stabilization device 10 is coupled to the eye, a gripper device 14, a lens cone 16 and an applanation lens 18, which in combination with the lens cone 16 is used to establish an appropriate optical path alignment between the cornea and a laser optical path.

The component parts of the stabilization device 10 are illustrated in exploded view, and are intended to be collapsed vertically, such that each of the individual portions of the device are in mechanical engagement with appropriate other portions, such that the completed device is provided in a generally unitary structure. This is not to say that the devices' component parts are permanently affixed to one another: indeed, the component parts are separable and interchangeable at will. Rather, the stabilization device 10 is intended to form a single composite interface structure between a human cornea and a surgical laser once the component parts have been aligned with a patient's eye and with respect to the laser delivery system, as will be described in detail below.

As illustrated in the exemplary embodiment of FIG. 1, the attachment ring 12 forms the mechanical interface between the anterior surface of a human cornea and the remaining structure of the stabilization device 10. The attachment ring 12 is constructed of a flexible, hypoallergenic material such as rubber, hypoallergenic plastic, silicone, or the like. The attachment ring 12 is substantially annular in shape, having a generally smooth exterior surface and a highly articulated and functional inner surface, as will be described in greater detail below. Being annular in shape, the attachment ring 12 necessarily defines an outer diameter (OD) and inner diameter (ID), with the inner diameter circumscribing a central target opening 13. The absolute value of its outer diameter is not particularly relevant to practice the principles of the present invention, but the value of the inner diameter is suitably chosen such that when the attachment ring 12 is placed over a patient's eye, the attachment ring's central opening, defined by the inner diameter, completely circumscribes a sufficient area of corneal tissue such that a surgical laser procedure may be completely performed within the exposed area without having to displace the attachment ring 12. The attachment ring 12 further includes an attachment fitting 44 which extends, in a radial direction, from the exterior surface of the attachment ring 12. The attachment fitting 44 may be coupled to a vacuum source (not shown) via coupler 45.

To reduce the amount of intraocular pressure caused by the application of the device 10 during operation, one approach known in the art is to have the device 10 not applanate the cornea when applied. Turning to FIG. 2, an illustration is shown of a non-applanating operation of the ocular stabilization device 10 to interface with the eye 34. The lens cone 16 is coupled to the gripper device 14 without contact between the applanation lens 18 and the corneal portion 34a of an eye 34 or with minimal contact, such as at point of first visible contact between the applanation lens 18 and the corneal portion 34a. In one embodiment, the lens cone 16 is coupled to the gripper device 14 such that the apex ring 30 of the lens cone 16 is partially lowered into engagement with the attachment ring 12. In the embodiment shown in FIG. 2, an inner surface 60 of the gripper portion 19 of the gripper device 14, an inner surface 73 of the attachment ring 12, an inner surface 70 of the receiver portion 20 of the gripper device 14, and the applanation lens 18 form a chamber 54. As the gripper portion 19 includes the jaws (not shown), the inner surface of the gripper portion 19 is coextensive with the inner surface of the jaws, in one embodiment. Based on the position of the lens cone 16, and thus the position of the applanation lens 18, within the gripper portion 19 as well as the placement of the attachment ring 12 on the ocular surface, the chamber 54 can be formed without the inner surface of the gripper portion. For example, when the lens cone 16 is positioned within the gripper portion 19 such that the apex ring 30 engages all of the inner surface 60 of the gripper portion 19 without engaging the inner surface 70 of the receiver portion 20, the chamber 54 is formed by the applanation lens 18, the inner surface 70 of the receiver portion 20, and the inner surface 73 of the attachment ring 12. Thus, the dimensions of the chamber 54 can vary with the position of the lens cone 16 within the gripper device 14 but are fixed once the jaws are compressed against the apex ring 30. Additionally, the chamber 54 is preferably not fluid-tight to allow displacement of the liquid material out of the chamber 54. In an exemplary embodiment of the present invention, a liquid is provided in the chamber 54 such that any output beam from the laser delivery tip traverses through the applanation lens 18 and through the liquid to the eye 34 (e.g., the corneal portion 34a or other structures of the eye 34, such as the capsular bag, the natural lens, and the like).

Referring to FIG. 2, when the stabilization device 10 to the eye 34, after the attachment ring 12 is suctioned to the eye 34, a receptacle is formed by the anterior surface of the cornea, the inner surface 70 of the receiver portion 20, and the inner surface 60 of the gripper portion 19. In operation, a liquid or otherwise flowable material is then provided in this receptacle (e.g., by drops, injection, or the like). The lens cone 16 is subsequently docked to the gripper device 19 and displaced towards the corneal portion 34a. Alternatively, the liquid or otherwise flowable material may be provided in the receptacle after the chamber 54 is formed, such as after the lens cone 16 has been docket to the gripper device 19.

The liquid or otherwise flowable material is preferably biocompatible with the ocular tissue and substantially transparent or has a refractive index that substantially matches the refractive index of the corneal portion 34a. The incorporation of the liquid or otherwise flowable material between the applanation lens 18 and the corneal portion 34a minimizes trajectory departure of the output beam from the laser delivery tip to the desired ocular tissue structure or at least provides relative predictability to determine the trajectory departure, if any. Examples of suitable liquids, fluid-like suspensions or other compositions include but are not necessarily limited to basic salt solution ("BSS"), ophthalmic viscoelastic device, and the like, and any combination of one or more of the foregoing.

FIG. 2 shows a non-applanating application of the ocular stabilization device 10 that is particularly suited to laser assisted ophthalmic surgical procedures where minimizing change to intraocular pressure is desirable, such as in cataract procedures in older patients or patients with glaucoma-related or diabetic related complications. As previously mentioned, the chamber 54 is not fluid-tight. The liquid or otherwise flowable material may be displaced out of the chamber 54, such as from displacement of the applanation lens 18 towards the corneal portion 34a, after the gripper device 14 is affixed to the eye 34 and the lens cone 16 is docked with the gripper portion 19. This minimizes any external pressure that might be applied on the corneal portion 34a (and thereby any corresponding increase in intraocular pressure) due to displacement of the lens cone 16, and thus displacement of the applanation lens 18, towards the corneal portion 34a with the liquid material between the applanation lens 18 and the corneal portion 34a. Preferably, the applanation lens 18 has a flat surface and is positioned approximately 0.5 mm above the apex of the cornea surface 34a. This may provide less distortion in the optical path to the cornea's 34a back surface as compared to having the applanation lens 18 make direct contact with the cornea 34a.

With this configuration, there is still some amount of additional intraocular pressure placed on the eye 34 caused by the downward force of the docked device 10. The downward force may range from 150-400 grams, depending on how much force is applied by the operator. This downward force is applied over the effective surface area of the interface between the device 10 and the eye 34, e.g., the suction ring 36. The increase in intraocular pressure resists these downward forces over this net effective area. However, reducing the downward force might compromise the torsional rigidity of the device 10 during operation, which may cause adverse outcomes.

Figure 3:
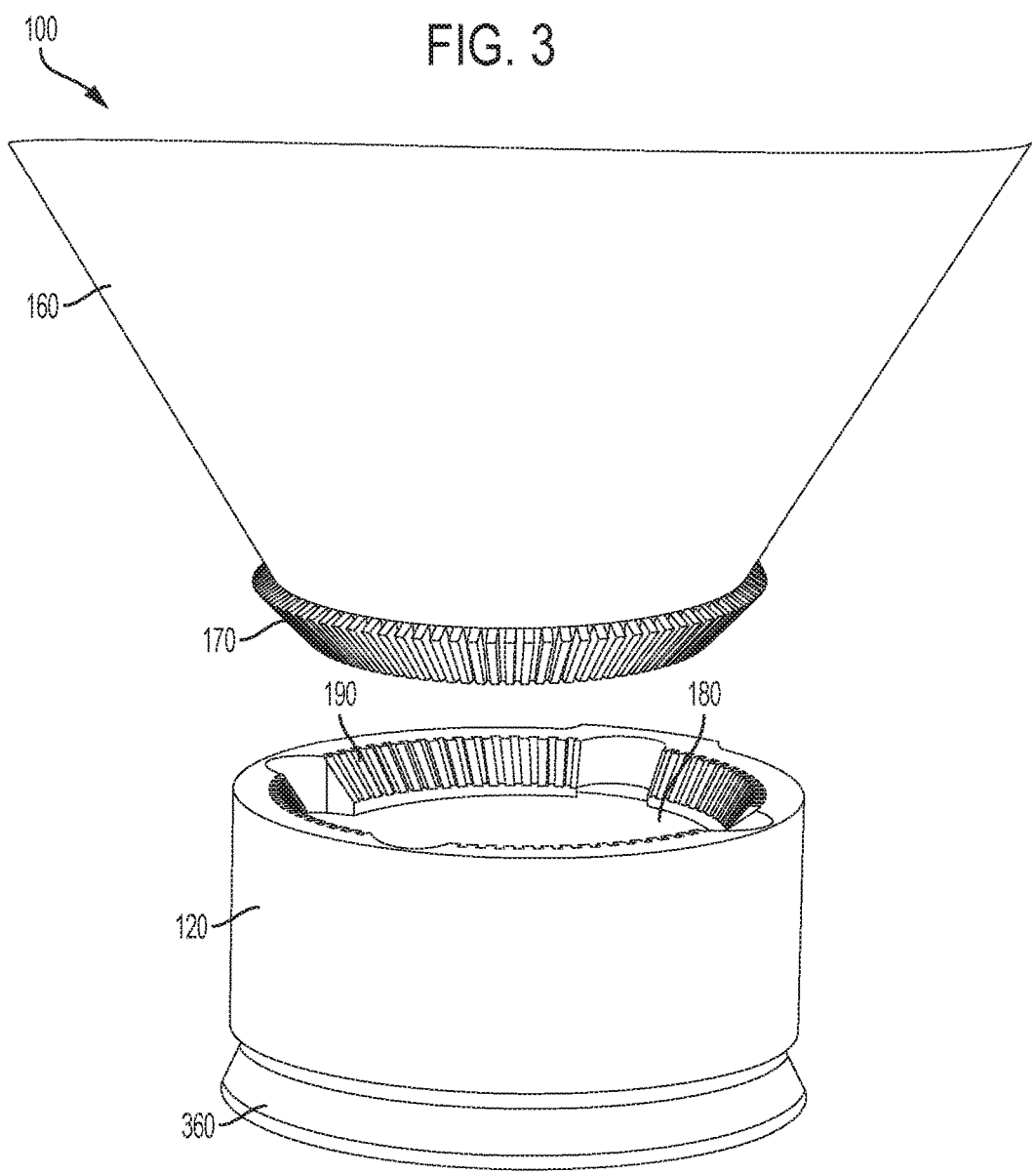
FIG. 3 is a perspective illustration of an ocular stabilization device in accordance with one embodiment of the present invention.

An approach to address these concerns is shown in FIG. 3, which illustrates a patient interface 100 in accordance with a preferred embodiment of the present invention. The patient interface 100 includes a lens cone 160 to establish an appropriate optical path alignment between the cornea and a laser optical path. The patient interface also includes an attachment ring 120. The surfaces of the mating interfaces between the cone 160 and the attachment ring 120 are splined (190 and 180, respectively), similar to a bevel gear with fine teeth, that would provide rotational locking and lateral fixation when the patient interface 100 is docked to the patient's eye.

In one preferred embodiment, not only could the required downward force be reduced, but the gripper device (e.g., gripper 14 in FIG. 2), could be removed from the configuration. This may further enable the operator to quickly lift the cone 160 away from the patient in the case of an unexpected event occurring.

Figure 4:
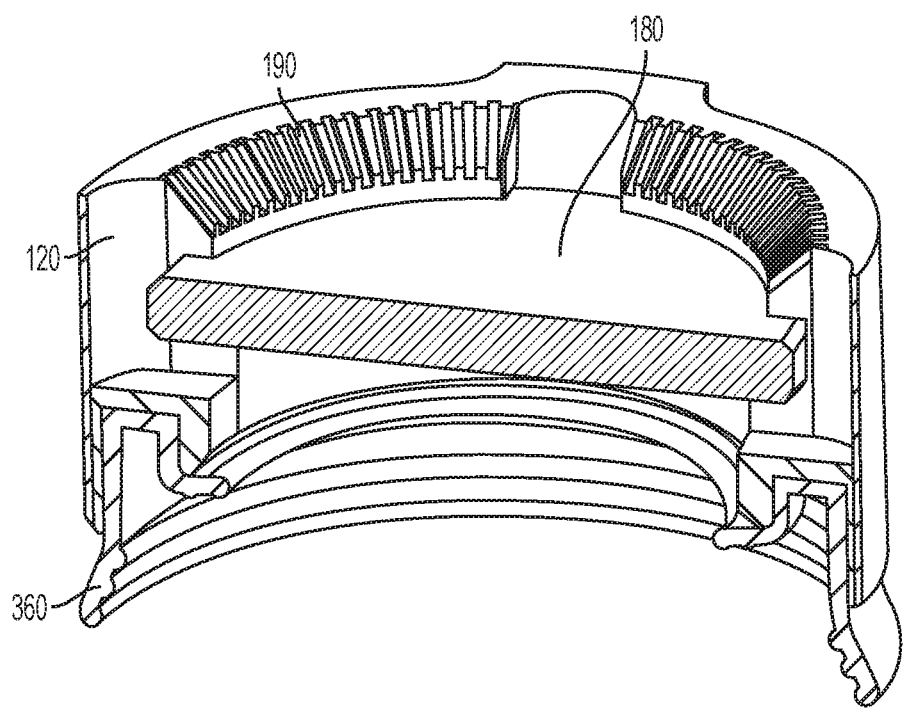
FIG. 4 is a cross-section view of an ocular stabilization device in accordance with one embodiment of the present invention.
Figure 5:
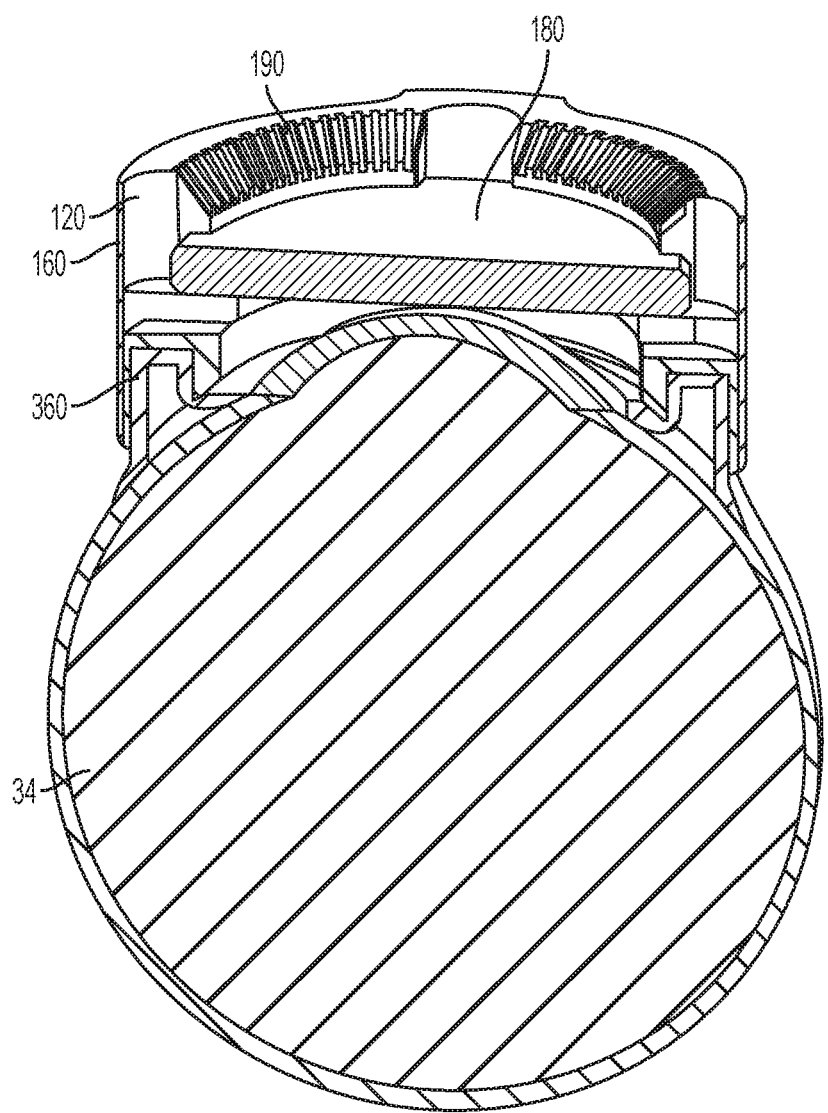
FIG. 5 is another cross-section view of an ocular stabilization device in accordance with one embodiment of the present invention.

Turning to FIG. 4, a cross section of the attachment ring 120 is shown. The attachment ring 120 includes lens 180, which is preferably a flat-glass surface that allows the laser beam access and visual access to the cornea 34*a* and surrounding area. In a preferred embodiment, the laser system using this patient interface 100 can detect the distance to the operation surfaces, e.g., the cornea 34*a*, ocular lens, etc. . . . This enables flexibility as to precise placement of the lens 180, which enables a more cost-effective design. Like the previous embodiments, a vacuum source (not shown) may be coupled to the chamber formed by the ring 120 and the eye's 34 surface to create a negative pressure that seals the chamber and applies axial force to the eye 34. Turning to FIG. 5, a cross section of the attachment ring 120 is shown attached to a patient's eye 34.

Figure 6:
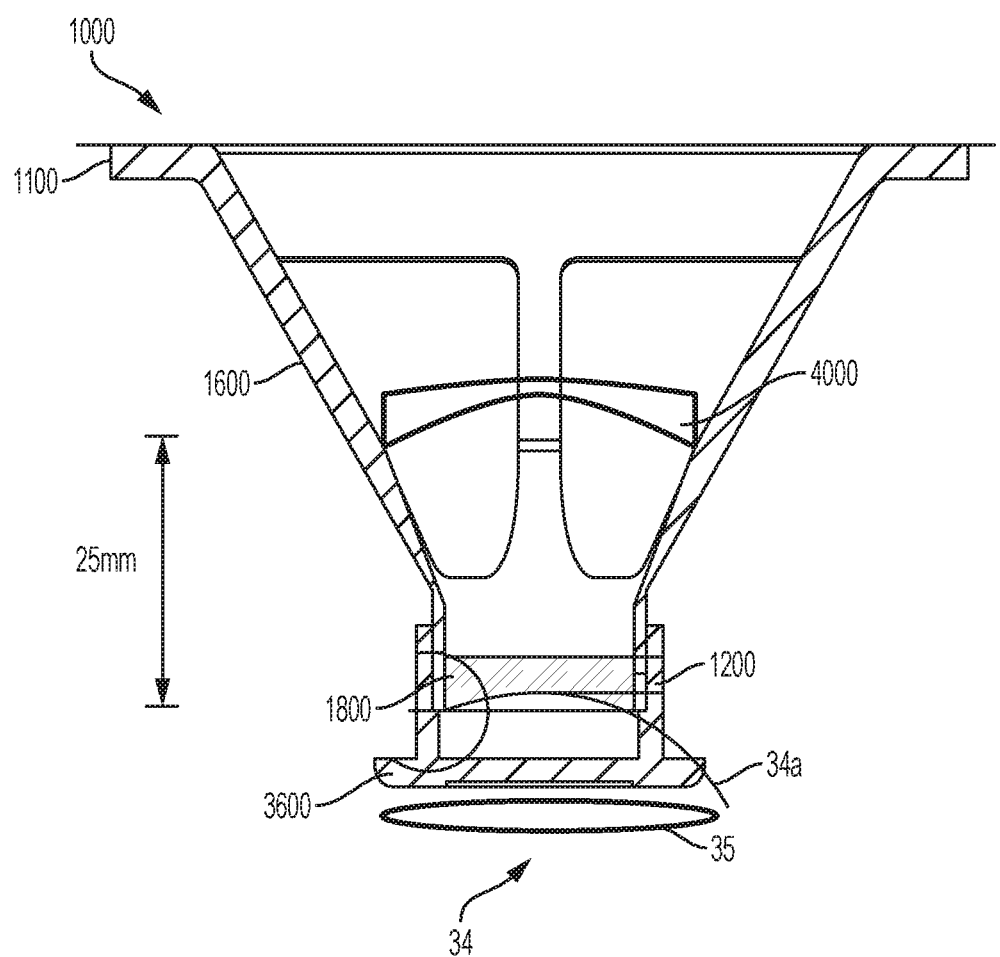
FIG. 6 is another cross-section view of an ocular stabilization device in accordance with one embodiment of the present invention.

Turning to FIG. 6, another exemplary patient interface is shown 1000. As with the previous embodiments, patient interface 1000 includes a lens cone body 1600. Generally, patient interfaces for laser systems configured to treat the corneal surface 34*a* of the eye 34 may have limited range of transversal and longitudinal magnification, thereby having a limited range of diameter and depth, respectively. For example, such a system may have a transversal magnification range of about 9.5 mm and a longitudinal magnification range of about 1.52 mm (just to reach the corneal tissue). However, for cataract surgery, the beam of such a system should preferably reach about 14-15 mm in diameter to account for the larger diameter of the lens 35 of the eye. The beam should also preferably reach about 2-4 mm in depth to reach across the eye's anterior chamber to the lens 35.

One approach to address this issue in shown in patient interface 1000. In this embodiment, lens 4000 is included in the patient interface 1000 located in the cone body 1600 above lens 1800 that makes direct contact with eye 34. The lens 1800 is located in the attachment ring 1200, which also coupled to a suction ring 3600. Preferably, the lens 4000 is located approximately 25 mm above the lens' 1800 contact with eye 34. Lens 1800 is preferably a negative lens—at least on the portion that contacts the eye 34 as shown in FIG. 6, to fit the shape of the corneal surface 34*a* and minimize applanation. The aspheric lens 4000 has a focal ratio, F, of about −73 mm. With this configuration, the transversal magnification can be increased by a factor of approximately 1.52 (73 mm/73-25). Thus, for a system with a 9.5 mm diameter range, the range may increase to 14.4 mm (1.52× 9.5). Moreover, the longitudinal magnification can be increased by a factor of 2.3 (1.52^2). Thus, for a system with a 1.3 mm depth (or L3 z range), the range can be increased to about 3 mm (1.3×2.3), thereby facilitating treatment of the lens 35 of the eye.

Figure 7:
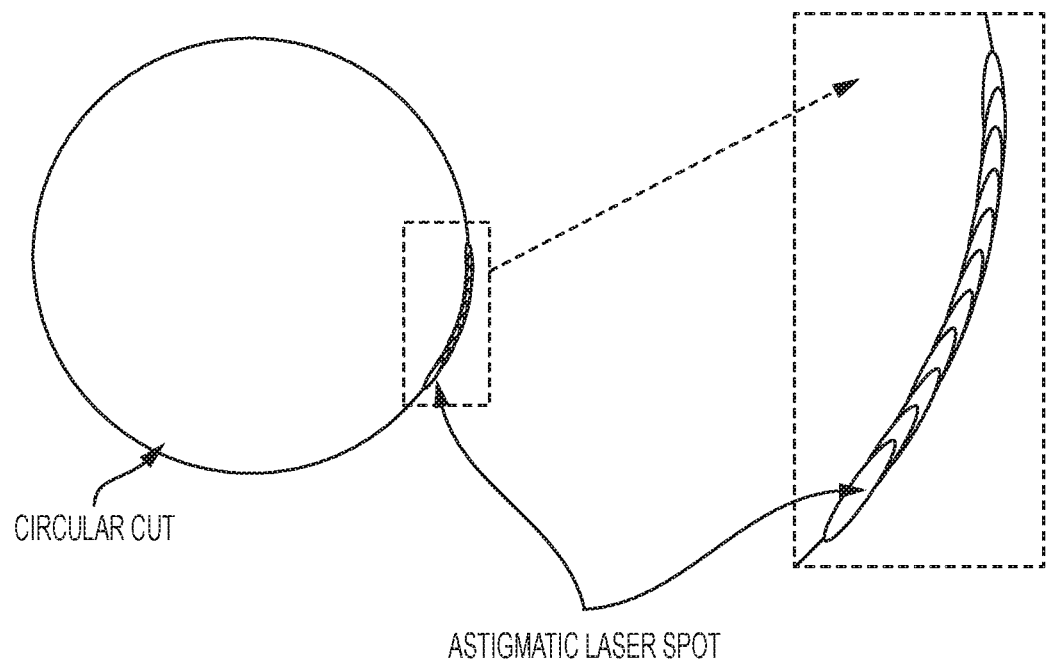
FIG. 7 is an illustration of the operation of one embodiment of the present invention.

Several advantages may be gained from this configuration. For example, no change would be necessary to the load dock interface 1100. Further, turning to FIG. 7, an example circular cut is shown, e.g., a circular cut in the capsular bag 35. Because the treatment beam in the configuration in FIG. 6 is further compressed by aspheric lens 4000, the laser spot forms an astigmatic shape in the tangential focal plane. This may create a desirable effect in forming a more precise circular cut.

Finally, to compensate for the compressed laser beam, it may be desirable to increase the length of the cone. For the configuration shown in FIG. 6, with the dimensions described above, an increase of about 13 mm in the length of the cone and interface 1000 may be preferable. This may be desirable for patients that have possible anatomical obstacles, e.g., the nose may be too closely situated to the treat eye 34 such that it interferes with the placement of the patient interface 1000, thereby causing an obstacle. A longer interface 1000 may facilitate an improved fit.

A number of exemplary embodiments suitable for practice of the present invention have been described in connection with various illustrations of FIGS. 1-7. However, it should be understood by those having skill in the art that certain modifications, simplifications and expansions may be made without departing from the spirit and scope of the present invention. Specifically, any appropriate laser medium might be used to deliver the incident laser beam without regard to the particular form and shape of the delivery system. In addition, the gripper structure need not be a unitary structure, for example, but may indeed be hinged in a central portion and the gripper jaws opened and closed in response to spring tension and compression made between the gripper handles. Likewise, the applanation lens need not be provided with a substantially flat applanation surface. Depending on the ophthalmic procedure intended to be carried out by the laser system, the lens's applanation surface may be concave or convex in accordance with an appropriate mathematically derived curvature, without departing from the scope and spirit of the invention.

In this particular regard, it will be understood that some degree of spherical aberration might be present in an uncompensated laser beam if the applanation lens were curved. However, given the mathematical characterizability of the curvature of the applanation surface, it should be understood that a laser beam can be focus-compensated in order to accommodate a degree of curvature.

Accordingly, it is to be understood that the foregoing embodiments are merely illustrative of the invention and that no limitations are intended to either the details of the construction or design other than as defined in the appended claims.

Support Ring for Use with a Suction Ring

Other embodiments of this invention are generally directed to a support ring for use with a suction ring of an intraocular device. The support ring has a central opening and at least a first end surface extending toward the central opening to define a concave curvature configured to match a curvature of a patient's eye. An outer surface of the support ring includes an annular groove formed adjacent the first end surface and a plurality of exterior vacuum channels spaced around the annular groove extending axially from the annular groove to a second end surface. The concave curvature in the first end surface of the support ring and the annular groove and exterior vacuum channels in the outer surface maximize flexibility of the sealing edges of the suction ring while decreasing relative deformation on the eye. As a result, the likelihood of eye deformation, intraocular pressure increase or rise, and blood vessel rupture is minimized.

FIG. 8 is an exploded, perspective view illustration of an ocular stabilization device 10 including a support ring 20 and other components. Although illustrated as being spaced apart from each other in FIG. 8, the components of the device 10 collapse vertically to mechanically engage and form a single unitary structure. The ocular stabilization device 10 attaches to the eye to provide a mechanical interface between the cornea and the laser surgical device and to minimize or prevent translational and rotational movement of the eye with respect to an incident beam of a laser surgical device.

According to an embodiment, the ocular stabilization device 10 includes a lens cone 12, an applanation lens 14, a gripper component 16, a suction or attachment ring 18, and the support ring 20. The lens cone 12 is configured to engage with the laser surgical device (not shown) and to maintain the applanation lens 14 and hence, a portion of the eye, a known distance from a delivery tip of the laser surgical device. The lens cone 12 is generally formed from a substantially rigid material, such as a molded plastic, metal material, and the like and includes a base ring 22 and an apex ring 24 that are separated from each other by support struts 26.

The base ring 22 is configured to attach to a distal end of the laser surgical device and is a substantially planar disk having an outer diameter, an inner diameter, a substantially flat end surface 28, and an opposite flat surface 30. In another embodiment, the base ring 22 is otherwise suitably shaped to engage with the laser surgical device. The apex ring 24 is generally smaller than the base ring 22 to provide the lens cone 12 with a truncated cone shape. In an example, the apex ring 24 is cylindrical and has an outer surface 32 and an inner surface 34 defining outer and inner diameters, respectively, that are less than the inner diameter of the base ring 22. In any case, the inner diameters of the base ring 22 and the apex ring 24 define openings that are suitably aligned and dimensioned to provide unobstructed passage for a laser beam, and the inner diameter of the apex ring 24 is suitably dimensioned to provide a receptacle for the applanation lens 14.

The struts 26 extend at an angle from an interior end 36 of the apex ring 24 outwardly toward the inner diameter of base ring 22. In an embodiment, the struts 26 attach to a skirt 40 extending from the base ring 22, which adds structural integrity to the lens cone 12. In another embodiment, the skirt 40 is omitted and the struts 26 attach directly to the inner diameter of the base ring 22. Although four struts 26 are illustrated as being spaced substantially evenly around the lens cone 12, fewer or more struts 26 are included and/or spaced unevenly around the lens cone 12 in another embodiment.

As alluded to briefly above, the applanation lens 14 is retained within the apex ring 24 and is configured to transmit light at a particular wavelength delivered by the laser delivery system to the eye. In an embodiment, the applanation lens 14 is constructed from a quartz silicate glass, an optical quality plastic, or another biocompatible transparent material. The applanation lens 14 is generally disk-shaped and has an outer diameter that is substantially equal or similar to the inner diameter of the apex ring 24. In an embodiment, an outer edge 42 of the applanation lens 14 includes engagement features (not shown), such as bumps or ridges, which operate to improve mechanical coupling with the apex ring 24. In another embodiment, the outer edge 42 of the applanation lens 14 is roughened or otherwise textured to improve adherence of an adhesive for bonding the lens 14 to the apex ring 24. The applanation lens 14 includes a substantially planar applanation surface 44, or alternatively, the applanation surface 44 is concave or otherwise shaped to match a contour of the anterior corneal surface.

The gripper component 16 provides an alignment and coupling interface between the lens cone 12 and the suction ring 20. In an embodiment, the gripper component 16 includes a gripper portion 46 for receiving a portion of the lens cone 12 and a receiver portion 48 coupled to the gripper portion 46 for containing the suction ring 18 and the support ring 20. With additional reference to FIGS. 9 and 10, the gripper portion 46 includes a jaw section 50 that has two jaws 52 and 54 surrounding a central opening 56 and a handle section 58 with two handles 60 and 62 extending from corresponding jaws 52 and 54. The handles 60 and 62 are separated by a gap 64 that narrows when the handles 60 and 62 are squeezed. As a result, a deformation force is transmitted from the handles 60 and 62 to the jaws 52 and 54 causing the central opening 56 to enlarge to a diameter sufficient for receiving the lens cone 12, specifically the apex ring 24. An optional latch 63 is included on one of the handles 60 and corresponds with a hook 65 on the other one of the handles 62 to prevent the jaws 52 and 54 from contracting when the apex ring 24 is being inserted into the central opening 56 during assembly. When the handles 60 and 62 are released and the latch 63 is unhooked, the jaws 52 and 54 contract and grasp the outer surface 32 of the apex ring 24 to temporarily attach the gripper portion 46 to the lens cone 12. In an embodiment, a cap 66 having an interior surface 68 corresponding to an outer surface 70 of the jaws 52 and 54 is included to bias the jaws 52 and 54 to the relaxed, contracted position.

The receiver portion 48 is substantially ring-shaped and is disposed alongside the jaws 52 and 54 of the gripper portion 46 in order to engage with the suction ring 18 and to align the suction ring 18 with the lens cone 12. In an embodiment, the receiver portion 48 includes an annular section 72 and an extension 76. The annular section 72 is dimensioned substantially similarly to the jaws 52 and 54 is connected to the gripper portion 46 via a connection piece 74. In an embodiment, the annular section 72 is formed as an annular receptacle. An inner surface 78 of the annular section 72 defines a central opening or orifice 80 that aligns with the central opening 56 of the jaws 52 and 54 and that is substantially equal to or slightly larger than the outer diameter of the suction ring 18.

Referring to FIG. 11, according to an embodiment, the inner surface 78 of the annular section 72 further includes retention features that are formed as part of or are provided by a separate component inserted into the annular section 72. In an embodiment, the retention features are made up of a retention ring defined by an outer annular wall 82, an inner annular wall 84 concentric to the outer annular wall 82, a bottom wall 86, and an annular channel 88 for receiving the suction ring 18. In such an embodiment, the outer annular wall 82 has a height that is greater than a height of the inner annular wall 84 so that the suction ring 18 can be friction fit with the annular channel 88. The extension 76 (FIGS. 9 and 10) extends radially outwardly from the annular section 72 and is made up of two spaced apart side walls 92 and 94 that define a guide channel 96 for retention of an attachment fitting 98 of the suction ring 18 by a compressive force. Retention of the suction ring 18 is enhanced by use of a suitable adhesive, in addition to the frictional forces, as alluded above.

With continued reference to FIG. 11, the suction ring 18 is configured to interface with the anterior corneal surface and has an outer annular wall 100, an inner annular wall 102, a radial wall 104, an annular cavity 106, and the attachment fitting 98. The annular cavity 106 receives the support ring 20 therein and distributes the vacuum pressure to the eye during laser surgery. The vacuum pressure is fed to the annular cavity 106 via the attachment fitting 98, which includes a port 108 extending therethrough. A free end of the attachment fitting 98 connects to the vacuum apparatus or a portion 109 thereof so that the vacuum pressure can be delivered to the suction ring 12 via the port 108.

In an embodiment, the outer annular wall 100 of the suction ring 18 has an outer diameter that is substantially equal to or slightly less than an inner diameter of the outer annular wall 82 of the receiver portion 48. Additionally, the inner annular wall 102 of the suction ring 18 has an inner diameter that is substantially equal to or slightly smaller than an outer diameter of the inner annular wall 84 of the receiver portion 48, thereby insuring that the suction ring 18 remains positioned within the annular channel 88.

To minimize disturbance to the eye during laser surgery, the suction ring 18 is constructed of a flexible hypoallergenic material. Suitable materials include, but are not limited to rubber, hypoallergenic plastic, silicone, and the like. Additionally, the outer annular wall 100 is configured to be taller than the inner annular wall 102 so that each of the top edges 122 and 124 of the walls 100 and 102 follow the contour of the eye when the suction ring 18 is disposed thereon.

In an embodiment, the outer annular wall 100 is greater in height than the outer annular wall 82 of the receiver portion 48 to thereby define a flexible shroud 110 that extends beyond the outer annular wall 82. The flexible shroud 110 has a generally curved surface and extends at an angle to extend radially outwardly from the outer annular wall 100. In an embodiment, the flexible shroud 110 extends from the outer annular wall 100 at about a 30 degree angle. Alternatively, the flexible shroud 110 is extends at another angle, for example, between about 15 degrees and about 45 degrees relative to the outer annular wall 100. The flexible shroud 110 has a curved outermost edge 112 and ridges 114 that serve as contact surfaces when the suction ring 18 is placed on the eye. An innermost one of the ridges 114 may be substantially rigid relative to outer ones of the ridges 114 to thereby maintain a substantially uniform inner diameter when the flexible shroud 110 deforms in response to pressure from contact with the eye. Although three ridges 114 are illustrated, fewer or more are included alternatively. The inner annular wall 102 includes a flexible lip 116 extending radially inwardly therefrom to thereby hang over the inner annular wall 84 of the receiver portion 48. The flexible lip 116 has a curved inner edge 120 and ridges 118 configured to serve as contact surfaces for the eye. Although two ridges 118 are depicted, more or fewer are included in other embodiments. The ridges 114 and 118 improve suction pressure with the corneal surface of the eye.

The support ring 20 is disposed within the annular cavity 106 of the suction ring 18 and is configured to prevent buildup of intraocular pressure when the ocular stability device 10 is placed on the eyeball. In this way, the device 10 can be more easily removed from the eyeball after completion of a laser surgery procedure. With additional reference to FIGS. 12 and 13, the support ring 20 is formed from flexible material, such as a plastic and the like, and has an annular groove 128, a plurality of exterior vacuum channels 130, a relatively wide contact end surface 132.

The annular groove 128 extends around an entirety of an outer surface 126 of the support ring 20. In an embodiment, the annular groove 128 receives the vacuum pressure from the port 108 during laser surgery and is thus formed adjacent the anterior end surface 134 opposite the contact end surface 132 of the support ring 20. The exterior vacuum channels 130 extend axially from the annular groove 128 along the outer surface 126 and are spaced evenly around the support ring 20. In an embodiment, the exterior vacuum channels 130 are formed substantially parallel to a central axis 137 extending through a central opening 138 of the support ring 20. Alternatively, one or more of the exterior vacuum channels 130 is formed at an angle relative to the central axis 137. Although six exterior vacuum channels 130 are illustrated, more or fewer exterior vacuum channels 130 are included in other embodiments.

Each exterior vacuum channel 130 aligns with a notch 140 formed in the anterior end surface 134. The notches 140 direct pressure from the exterior vacuum channels 130 to an inner surface 136 of the support ring 20. Although illustrated as being generally rectangular, the notches 140 alternatively are semi-circular, semi-ovular, or another shape. Additionally, although six notches 140 are illustrated as being included in support ring 20, more or fewer are included in other embodiments.

The contact end surface 132 is configured to rest against the eye and has a width that is greater than a width of the anterior end surface 134. When inserted into the suction ring 18, the contact end surface 132 is sufficiently wide to extend from the outer annular wall 100 to the inner annular wall 102. In an embodiment, the contact end surface 132 curves from the outer surface 126 of support ring 20 to the inner surface 136 in a concave manner to substantially match a curvature of the eye.

To enhance frictional forces with the cornea when the contact end surface 132 is in contact with the eye, the contact end surface 132 is textured so that when vacuum pressure is supplied to form a seal between the suction ring 18 and the eye, the sealing area is divided into a plurality of small sealing areas. In an example, the contact end surface 132 includes raised or depressed features. In an embodiment, the contact end surface 132 includes an annular groove 143 and a plurality of radially outward extending grooves 145 intersecting the annular groove 143 at various locations to form the various sealing areas. The annular groove 143 is formed halfway between the outer and inner surfaces 126 and 136 of the support ring 20, in an embodiment or, alternatively, is formed closer to one surface 126 or 136 than the other. The radially outward extending grooves 145 are substantially evenly spaced around the contact end surface 132 and are angled substantially perpendicularly relative to the annular groove 143. Alternatively, the radially outward extending grooves 145 are non-perpendicular relative to the annular groove 143 and unevenly spaced around the contact end surface 132. Generally, the radially outward extending grooves 145 are substantially identically configured width- and depth-wise. Although a single annular groove 143 and eighteen radially outward extending grooves 145 are illustrated as being on the contact end surface 132, alternatively, more or fewer annular grooves 143 and/or radially outward extending grooves 145 can be included.

To further manipulate pressure distribution around the eye, selected ones of the radially outward extending grooves 145 that communicate with corresponding exterior vacuum channels 130 have widened outer mouths 146. According to an embodiment, each outer mouth 146 is about three to four times wider than the width of a main portion of its groove 145. In another embodiment, the selected radially outward extending grooves 145 also include a widened inner mouth 148. The widened inner mouth 148 is substantially equal in dimension to its corresponding widened outer mouth 146, in an embodiment. In another embodiment, the inner mouth 148 is narrow or wider than the outer mouth 146. Although six grooves 145 are shown with widened mouths 146 and 148, alternatively, more or fewer include outer and/or inner mouths 146 and/or 148.

The inner surface 136 of the support ring 20 is shaped to match the contour of a portion of the inner annular wall 102 of the suction ring 18. In an embodiment, the inner surface 136 is generally concave and has an annular ridge 152 extending radially inwardly in a curved manner from a narrow annular rim 154 toward the central opening 138. In another embodiment, the inner surface 136 includes a plurality of interior vacuum channels 150 and each aligns with a corresponding notch 140 and selected radially outwardly extending grooves 108. The interior vacuum channels 150 are formed on the annular ridge 152 and initiate at the rim 154. Each interior vacuum channel 150 is substantially equal to or similar in width as its corresponding notch 140. Alternatively, the interior vacuum channel 150 is wider or narrower than its corresponding notch 150. According to an embodiment, each interior vacuum channel 150 defines a portion of the inner widened mouths 148 of the radially outward extending grooves 145. Hence, in an embodiment in which six radially outwardly extending grooves 145 have widened mouths 148, six interior vacuum channels 150 are included. In other embodiments, more or fewer interior vacuum channels 150 are formed in the support ring 20.

During use, the support ring 20 is retained within the suction ring 18. Returning to FIG. 11, the support ring 20 is inserted into the annular cavity 106 of the suction ring 18 such that the anterior end surface 134 contacts the radial wall 104 to divide the cavity 106 into an outer portion and an inner portion. To insure that the support ring 20 does not become repositioned within the cavity 106, an adhesive or other material bonds the anterior end surface 134 to the radial wall 104. The coupled suction ring 18 and support ring 20 assembly is then ready for use with the ocular stability device 10.

FIG. 14 is a flow diagram of a method 700 of interfacing an eye during a laser surgery, according to an embodiment. In an embodiment, an ocular stabilization device (e.g., device 10) is provided at 702. For example, the ocular stabilization device 10 is pre-assembled and includes the suction ring 18 and support ring 20 assembly temporarily coupled to the gripper component 16, the applanation lens 14, and lens cone 12. Alternatively, the components of the ocular stability device 10 are provided separately and one or more of the components need to be assembled together. In the case in which the device is to be assembled, the to-be-assembled components include the lens cone 12, the applanation lens 14, the gripper component 16, the suction ring 18, and the support ring 20. In an embodiment in which the applanation lens 14 is not already attached to the lens cone 12, the lens 14 is inserted into the apex ring 24 of the lens cone 12. According to an embodiment, the lens 14 is maintained in position within the apex ring 24 via grooves and press fit therein, adhered via an adhesive, or otherwise mechanically coupled to the apex ring 24.

The handles 60 and 62 of the gripper component 16 are squeezed to enlarge its central opening 56, and the apex ring 24 of the lens cone 12 is inserted into the enlarged opening 56. After the apex ring 24 is appropriately positioned, the handles 60 and 62 are released to temporarily couple the lens cone 12 to the gripper component 16. The suction ring 18 and support ring 20 assembly is inserted into a receiver portion 48 of the gripper component 16 (on a side opposite the apex ring 24). In some embodiments, the support ring 20 is not pre-assembled as part of the suction ring 18 and thus, the components are assembled, and then attached to the gripper component 16.

After assembly, the device 10 is positioned over the patient's eye at 704. For example, as shown in FIG. 15, the device 10 is disposed such that the iris or pupil of the eye 800 is substantially centered within the suction ring 18 and the applanation lens 14 is contacted with the cornea. In an embodiment, the suction ring 18 is placed around the limbus of the eye 800 such that the shroud 110 surrounds the anterior surface of the cornea thereby leaving optical access to the cornea. Alternatively, the shroud 110 is suitably configured to also surround a portion of the sclera of the eye 800. A compressive force is applied to the device 10, and hence, the applanation lens 14, the suction ring 18, and the support ring 20, to flatten the cornea, to deform the shroud 110 in an outwardly direction, and to allow the shroud 110 and the lip 114 to conform to the orb-like shape of the eye 800. A slight vacuum pressure is provided at 706 by a vacuum source or suction pump and is coupled to the suction ring 18 via the attachment fitting 98. The vacuum pressure is directed to the annular groove 106, which causes a vacuum seal to form between the eye 800 and the suction ring 18 (and hence, the support ring 20). In this way, the eye 800 is prevented from movement in vertical, horizontal, and other directions. After the eye is suitably fixed in position, the laser surgery procedure can be performed at 708. Post-surgery, the vacuum pressure is cut off and the device 10 is removed at 710.

The inclusion of the support ring 20 in the annular groove 106 of the suction ring 18, improves stabilization of the eye when a vacuum is supplied to the annular groove 106 because the support ring 20 exerts an additional fixation force against the eye 800 to help maintain the eye 800 in position. Additionally, since the support ring 20 divides the supply of vacuum pressure into segments, e.g., via the anterior end surface 132 dividing the annular groove 106 into inner and outer portions and distribution of the vacuum pressure through a plurality of exterior and interior vacuum channels 130 and 150, the seal with the eye 800 is formed from a plurality of small suction contact areas rather than a single, large, annular area. Moreover, the seal formed with the eye 800 quickly weakens when the vacuum supply is cut off. As a result, intraocular pressure is reduced when the device 10 is affixed to the eye 800 during laser surgery, which thereby minimizes the possibility of eye injury and reduces patient recovery time.

While at least one exemplary embodiment has been presented in the foregoing detailed description of the inventive subject matter, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the inventive subject matter. It being understood that various changes may be made in the function and arrangement of elements described in an exemplary embodiment without departing from the scope of the inventive subject matter as set forth in the appended claims.

What is claimed is:

1. A support ring for use with a suction ring of an ocular stability device, the support ring comprising:
   a first end surface;
   a second end surface opposite the first end surface having a width that is greater than a width of the first end surface, the second end surface extending toward a central opening in the support ring to define a concave curvature configured to substantially match a curvature of a patient's eye; and
   an outer surface extending between the first end surface and the second end surface, the outer surface including an annular groove formed adjacent the first end surface and a plurality of exterior vacuum channels spaced around the annular groove and extending axially from the annular groove to the second end surface, wherein the first end surface includes a plurality of notches each radially aligned with a corresponding one of the plurality of exterior vacuum channels.

2. The support ring of claim 1, wherein the second end surface is configured to enhance frictional forces between the support ring and the patient's eye when the second end surface is in contact with the patient's eye.

3. The support ring of claim 1, wherein each notch of the plurality of notches is substantially equal in width to the corresponding one of the plurality of exterior vacuum channels.

4. The support ring of claim 1, further comprising an inner surface opposite the outer surface and including a plurality of interior vacuum channels each aligned with a corresponding notch of the plurality of notches.

5. The support ring of claim 4, wherein at least a portion of the inner surface is concave.

6. A support ring for use with a suction ring of an ocular stability device, the support ring comprising:

a first end surface;

a second end surface opposite the first end surface having a width that is greater than a width of the first end surface, the second end surface extending toward a central opening in the support ring to define a concave curvature configured to substantially match a curvature of a patient's eye; and an outer surface extending between the first end surface and the second end surface, the outer surface including a first annular groove formed adjacent the first end surface and a plurality of exterior vacuum channels spaced around the first annular groove and extending axially from the first annular groove to the second end surface, wherein the second end surface includes a plurality of radially outwardly extending grooves each aligned with a corresponding one of the plurality of exterior vacuum channels and a second annular groove, the plurality of radially outwardly extending grooves intersecting the second annular groove.

7. The support ring of claim 6, wherein each groove of the plurality of radially outwardly extending grooves includes a widened outer mouth in communication with the corresponding one of the plurality of exterior vacuum channels.

8. The support ring of claim 7, wherein each groove of the plurality of radially outwardly extending grooves includes a widened inner mouth opposite the widened outer mouth.

9. The support ring of claim 6, wherein the inner surface includes an annular ridge, and the plurality of interior vacuum channels initiate at and extend radially inwardly along the annular ridge.

10. An ocular stability device comprising:

a suction ring including an outer annular wall, an inner annular wall, a radial surface extending between the outer annular wall and the inner annular wall, the outer annular wall, the inner annular wall, and the radial surface defining a cavity, and a tube extending radially outwardly from the outer annular wall defining an orifice in communication with the cavity; and a support ring disposed in the cavity, the support ring defining a central opening and including:

a first end surface;

a second end surface opposite the first end surface having a width that is greater than a width of the first end surface, the second end surface extending toward the central opening of the support ring with a concave curvature configured to substantially match a curvature of a patient's eye; and an outer surface extending between the first end surface and the second end surface, the outer surface including an annular groove and a plurality of exterior vacuum channels, the annular groove being formed adjacent the first end surface in communication with the orifice, and the plurality of exterior vacuum channels being spaced around the annular groove and extending axially from the annular groove to the second end surface, wherein the first end surface includes a plurality of notches each radially aligned with a corresponding one of the plurality of exterior vacuum channels.

11. The ocular stability device of claim 10, wherein the first end surface of the support ring contacts an interior-facing portion of the radial surface of the suction ring.

12. The ocular stability device of claim 10, wherein the second end surface of the support ring is textured.

13. The ocular stability device of claim 10, wherein the plurality of notches extend axially inwardly from the first end surface toward a corresponding one of the plurality of exterior vacuum channels.

14. The ocular stability device of claim 13, wherein the support ring further includes an interior surface including a plurality of interior vacuum channels each aligned with a corresponding notch of the plurality of notches.

15. The ocular stability device of claim 14, wherein at least a portion of the interior surface is concave.

16. The ocular stability device of claim 15, wherein the interior surface includes an annular ridge, and the plurality of interior vacuum channels initiate at and extend along the annular ridge.

17. The ocular stability device of claim 10, further comprising a gripper component including an annular receptacle receiving the suction ring and defining a central orifice.

18. The ocular stability device of claim 17, further comprising a lens cone including an apex ring, a base ring spaced apart from and having a diameter larger than a diameter of the apex ring, and struts extending between the apex ring and the base ring, wherein the apex ring is disposed in the central orifice of the gripper component.

* * * * *